(12) United States Patent
McCue et al.

(10) Patent No.: US 6,506,216 B1
(45) Date of Patent: Jan. 14, 2003

(54) TIBIAL TRAY WITH ADJUSTABLE KEEL

(75) Inventors: Diana F. McCue, Pocasset; Scott E. Dutiel, Franklin, both of MA (US)

(73) Assignee: Depuy Products, Inc., Warsaw, IN (US)

( * ) Notice: Subject to any disclaimer, the term of this patent is extended or adjusted under 35 U.S.C. 154(b) by 22 days.

(21) Appl. No.: 09/595,190

(22) Filed: Jun. 16, 2000

Related U.S. Application Data

(63) Continuation of application No. 09/076,967, filed on May 13, 1998.

(51) Int. Cl.[7] .................................................. A61F 2/38
(52) U.S. Cl. ................................. 623/20.34; 623/20.14
(58) Field of Search ........................... 623/20.14–20.34

(56) References Cited

U.S. PATENT DOCUMENTS

| | | | |
|---|---|---|---|
| 4,728,332 A | * 3/1988 | Albrektsson | 623/20 |
| 4,944,757 A | 7/1990 | Martinez et al. | 623/20 |
| 5,271,737 A | 12/1993 | Baldwin et al. | 623/20 |
| 5,290,313 A | 3/1994 | Heldreth | |
| 5,480,445 A | * 1/1996 | Burkinshaw | 623/20 |
| 5,879,391 A | * 3/1999 | Slamin | 623/20 |

FOREIGN PATENT DOCUMENTS

| | | | | |
|---|---|---|---|---|
| FR | 2665073 | * | 1/1992 | 623/20 |
| FR | 2 748 389 | | 11/1997 | |

\* cited by examiner

Primary Examiner—Corrine McDermott
Assistant Examiner—Alvin Stewart
(74) Attorney, Agent, or Firm—Nutter McClennen & Fish LLP

(57) ABSTRACT

A tibial prosthesis includes a tibial platform having a medial-lateral center and an inferior surface matable with a resected proximal tibia, and a modular keel that is fixable to the inferior surface and adjustable in a medial-lateral direction with respect to the medial-lateral center of the tibial platform.

12 Claims, 5 Drawing Sheets

TIBIAL TRAY WITH ADJUSTABLE KEEL

CROSS-REFERENCE TO RELATED APPLICATIONS this application is a continuation of Ser. No. 09/076,967 filed May 13, 1998.

Not Applicable.

STATEMENT REGARDING FEDERALLY SPONSORED RESEARCH

Not Applicable.

FIELD OF THE INVENTION

The present invention relates to a tibial prosthesis having a tibial platform and a modular keel that is adjustable in a medial-lateral direction with respect to the platform.

BACKGROUND OF THE INVENTION

Total knee arthroplasty involves implantation of new articulating surfaces for the tibia, femur and patella. The most common technique for providing new articulating surfaces for the tibia involves resecting an upper portion of the tibia then attaching a prosthetic implant to the tibia over the resected surface. A typical tibial implant includes a tibial tray adapted to abut the resected surface of the tibia and a bearing portion which includes the new tibial articulating surfaces. The tibial tray has a shape that is adapted to generally approximate the shape of the resected surface of the tibia so that the implant generally aligns with the resected surface when the tray is properly attached to the tibia.

The tibial implant may also include a stem and a keel. The keel extends from an inferior surface of the tray into the patient's bone so as to provide both fixation and positional stability. The stem extends from the inferior surface of the tray or from an inferior surface of the keel into the central canal of the patient's tibia.

In many tibial prostheses the stem and keel extend from a central position in the base. For some patients however the central canal of the tibia is not located centrally with respect to the tibial articulating surfaces. With these patients, orthopedic surgeons must undertake additional positioning steps to ensure that the tibial prosthesis is properly seated and that it articulates properly with the femoral prosthesis. This problem can be particularly acute in revision surgery where an existing tibial prosthesis is being removed and a new tibial prosthesis is being implanted. When the original tibial prosthesis is removed in revision surgery, often portions of the tibia to which the prostheses are attached become damaged during the removal process or lack viable bony support for the replacement tibial prosthesis. It therefore becomes necessary to attach the new prosthesis farther down into the central canal of the patient's tibia than the original prosthesis. In revision surgery a long stem is typically used with the tibial prosthesis to ensure good distal fixation of the prosthesis within the canal. The use of long stems however exacerbates positioning problems for patients whose anatomic canal is not centrally located with regard to the tibial articulating surfaces, potentially forcing the surgeon to compromise coverage of the resected tibia.

Accordingly, a need exists for tibial prostheses with keel and stem portions that can be variably positioned in the medial-lateral direction in order to provide the best possible fit for tibial prostheses for patients whose anatomic canal deviates from standard locations with respect to the tibial articulating surfaces, particularly for use in revision surgery. U.S. Pat. No. 5,271,737 discloses a tibial prosthesis with an offset stem. This stem however is fixed in position and is not adjustable. Accordingly, it won't provide the best possible fit for patients whose tibial canal deviates from the dimensions of this tibial prosthesis. There still exists a need for a tibial prosthesis with an adjustable keel that will allow surgeons the flexibility to treat patients whose tibial canal may not only be not centered but which might be offset in the medial-lateral direction by an unknown amount.

SUMMARY OF THE INVENTION

The present invention provides a tibial prosthesis having a tibial platform with a medial-lateral center and an inferior surface matable to a resected proximal tibia. A modular keel is fixable to the inferior surface of the platform and is adjustable in a medial-lateral direction with respect to the medial-lateral center of the tibial platform.

The tibial platform may include at least one slot extending in a medial-lateral direction with at least one mating element extending through the at least one slot to secure the modular keel to the tibial tray at a preselected offset from the medial-lateral center of the tibial tray.

In an alternative embodiment, the tibial prosthesis may include a rotating disc that is fixed at its center to the medial-lateral center of the tibial tray. The disc may further be fixed to the modular keel at a position on the disc that is offset from the center of the disc. The rotating disc may then be oriented to provide a preselected medial-lateral offset between the medial-lateral center of the tibial tray and the modular keel.

In a further embodiment, the modular keel has a preselected offset in a medial-lateral direction with respect to the medial-lateral center of the tibial platform. This modular keel may be selected from a group comprising a plurality of modular keels having different preselected offsets in a medial-lateral direction with respect to the medial-lateral center of the tibial platform.

The tibial prosthesis may also include a stem receivable within the central canal of a patient's tibia. The stem may be integrally formed with the modular keel, or the stem may be modular and matable with the keel.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
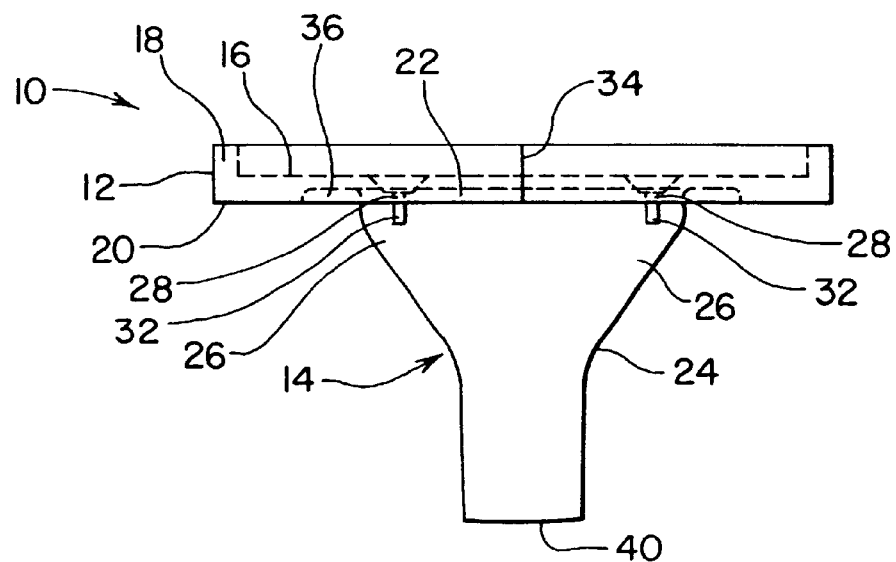
FIG. 1 is an anterior view of a tibial prosthesis of the invention having an adjustable keel.
Figure 2:
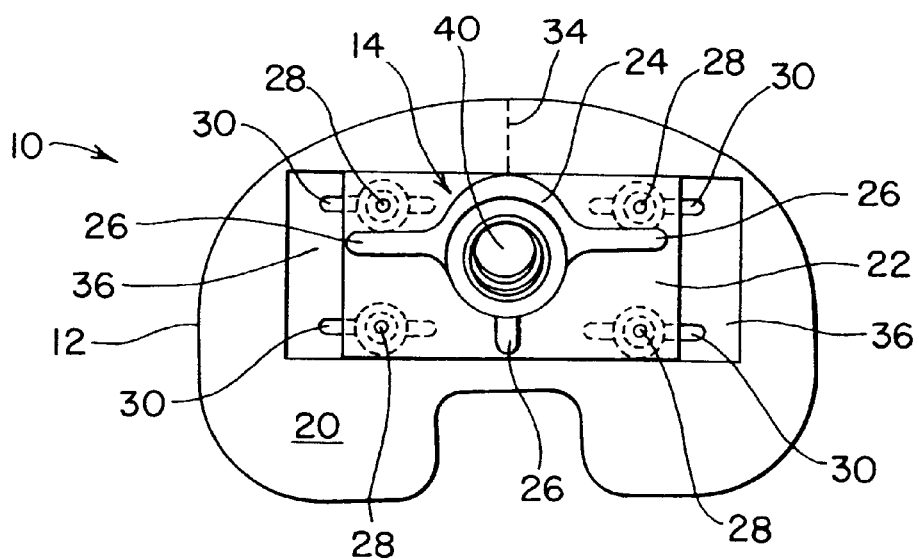
FIG. 2 is an inferior view of the tibial prosthesis of FIG. 1.
Figure 3:
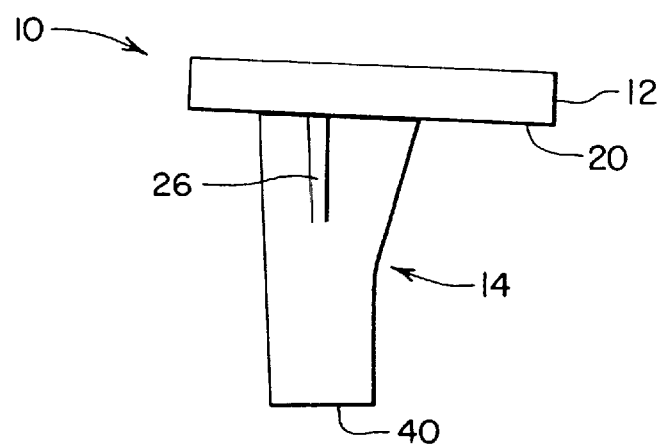
FIG. 3 is a side view of the tibial prosthesis of FIG. 1.

A tibial prosthesis 10 of the invention, illustrated in FIGS. 1 to 3, includes a tibial tray 12 or platform and a modular keel 14. The tibial tray 12 has a superior surface 16 defining a central tibial plateau region bounded by a peripheral rim 18. The tibial tray 12 has an inferior surface 20, opposed to the superior surface 16, that is generally shaped to mate with a proximal portion of a tibia that has been surgically resected for the purpose of executing a total knee arthroplasty. The superior surface 16 is designed to mate with a tibial bearing member (not shown). A variety of means for attaching a bearing member to a tibial tray are well known in the art and the present invention is not particularly limited to a specific bearing member or means for mounting a bearing member on the tray 12. The tray 12 and the modular keel 14 are preferably formed from a metal useful for prosthesis applications such as stainless steel or metal alloys, including titanium alloys.

A modular keel 14, matable to the inferior surface 20 of the tibial tray 12, has a superior, tray mating portion 22 and a keel portion 24. As illustrated in FIGS. 1 to 3, the keel portion 24 includes wing elements 26 extending in the medial, lateral and posterior directions. In other embodiments, the number and shape of the wing elements, as well as the angles at which they extend, may vary.

Modular keel 14 includes four threaded apertures 28 on its superior, tibial tray mating portion 22 that correspond to four slots 30 on the tibial tray 12. The slots 30 on the tibial tray 12 are elongate in a medial-lateral direction and are arranged so that when mating elements, such as screws 32, are inserted through each of the slots 30 to engage threaded holes 28, the modular keel 14 may slide in a medial-lateral direction with respect to the tibial tray 12 as the mating elements slide in the elongate slots 30. The slots 30 may be chamfered or have other means to permit the screws 32 to be seated at or below the superior surface 16 of the tibial tray 12 so that the screws 32 do not interfere with the positioning of a tibial bearing member. Generally, the slots 30 allow the modular keel 14 to be adjusted to provide a medial-lateral offset of up to at least about 8 millimeters in the medial or lateral direction from a medial-lateral center 34 of the tibial tray 12.

Tibial tray 12 may also include a recessed region 36 on its inferior surface 20. The recessed region 36 is generally of the same shape as the tray mating portion 22 of the keel. 14, but is elongated in the medial-lateral direction so that when the tray mating portion 22 is placed within the recessed region 36, adjustability of the modular keel 14 is limited to the medial-lateral direction. Preferably, the depth of recessed region 36 is equal to the thickness of tray mating portion 22 of the modular keel 14 so that the inferior surface 38 of the tray mating portion 22 is flush with the inferior surface 20 of the tray 12.

Figure 4:
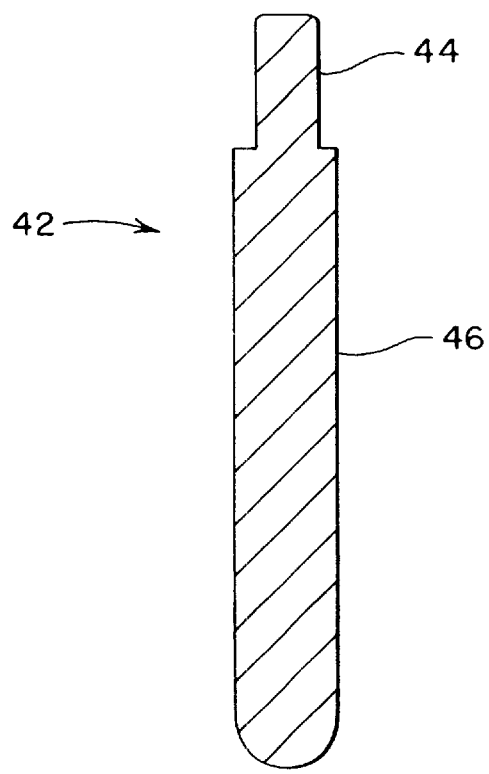
FIG. 4 is a cross sectional view of modular stem useful with the tibial prosthesis of the invention.

The illustrated modular keel 14 also includes a generally cylindrical stem mating element 40 defining an aperture having internal threads designed to mate with a modular stem component 42 (FIG. 4). A person of ordinary skill in the art will recognize that a modular keel 14 of the invention may include an integral stem, or may provide other means for the modular keel 14 to mate with a modular stem 42, such as by forming a taper interlock between male and female tapered surfaces in place of threads located on the modular keel 14 and stem 42.

A modular stem 42, as shown in FIG. 4, includes a mating portion 44 and a fixation portion 46. The fixation portion 46 is elongate and generally cylindrical and may be attached to the central canal of a tibia using bone cement or non-cemented methods. Generally, for revision procedures, long stems which extend into the isthmus of the tibial canal are used. Typical cemented long stem embodiments have a length ranging from about 30 to 60 millimeters, while non-cemented stem embodiments have a length ranging from about 75 to 150 millimeters.

Figure 5:
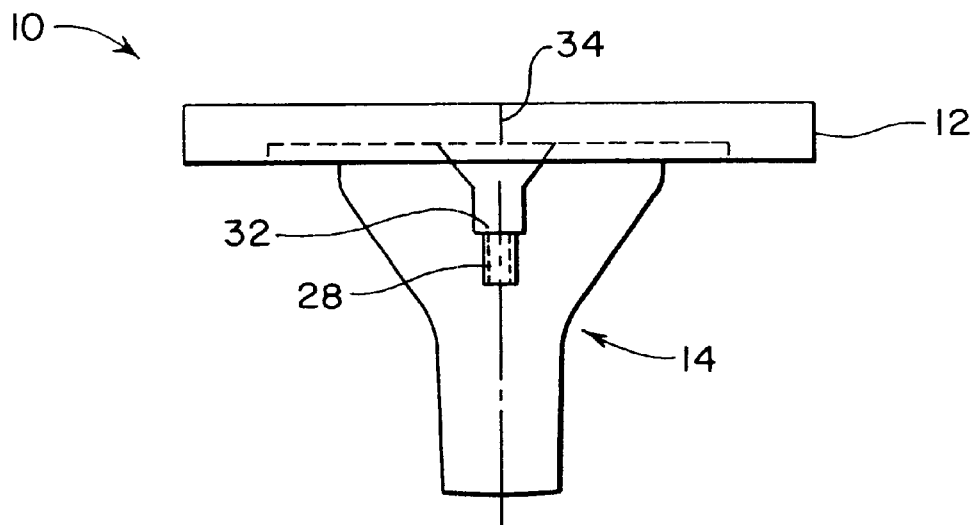
FIG. 5 is an anterior view of an additional tibial prosthesis of the invention having an adjustable keel.
Figure 6:
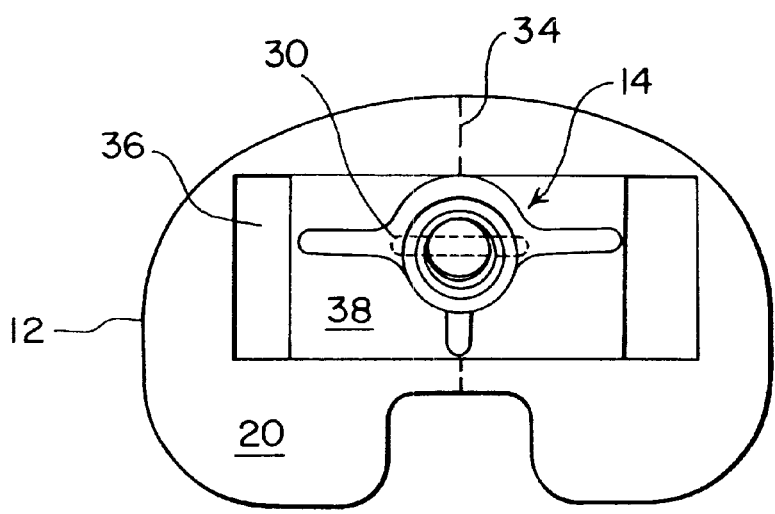
FIG. 6 is an inferior view of the tibial prosthesis of FIG. 5.
Figure 7:
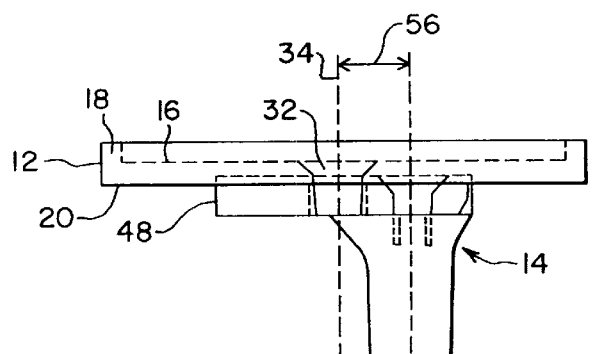
FIG. 7 is an anterior view of a further tibial prosthesis of the invention having an adjustable keel attached to a rotating disc.

In a further embodiment, shown in FIGS. 5 and 6, the modular keel 14 may be adjustably attached to the tibial tray 12 using a single mating element 32. In this embodiment, the tibial tray 12 includes a single slot 30 and the modular keel 12 includes a single threaded aperture 28 for attachment to the tibial tray 12. In general, the number of mating elements 32 may be varied by a person of ordinary skill in the art in keeping with the spirit of the invention.

Figure 8:
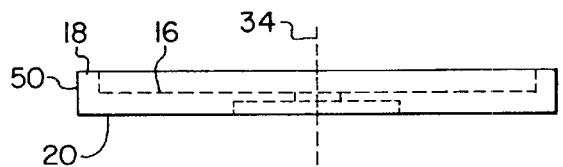
FIG. 8 is an anterior view of an asymmetric tibial tray useful with the prosthesis of FIG. 7.
Figure 10:
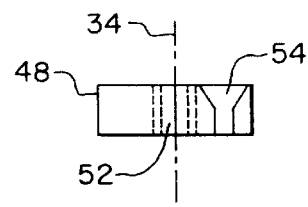
FIG. 10 is an anterior view of the rotating disc of FIG. 7.
Figure 9:
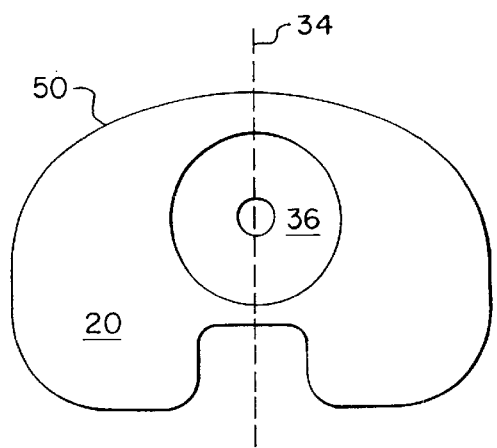
FIG. 9 is an inferior view of the tibial tray of FIG. 8.
Figure 11:
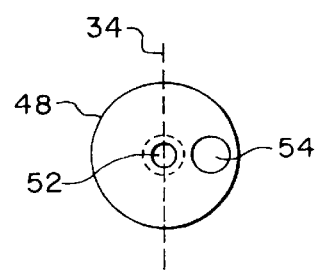
FIG. 11 is an inferior view of the rotating disc of FIG. 10.

As shown in FIGS. 7 to 11, medial-lateral adjustability of the modular keel 14 may also be provided using a rotating disc 48. In this embodiment, a rotating disc 48 is attached to the inferior surface 20 of tibial tray 12 (an asymmetric tibial tray 50 usable with the invention is illustrated in FIGS. 8 and 9) by a mating element, in this case a screw 32. The rotating disc 48 has a central aperture 52, for mating with the screw 32 and may be rotated about the central aperture 52 at least before the screw 32 is tightened. An offset aperture 54 is spaced apart from the central aperture 52 and seats a mating element, such as screw x, through the offset aperture 54 to attach the modular keel 14 to the rotating disc 48. In use, the modular keel 14 is attached to the rotating disc 48 at the second aperture 54, the rotating disc 48 is rotationally oriented so that the modular keel 14 extends at the desired medial-lateral offset 56, and the rotating disc 48 is fixed to the inferior surface 20 of tibial tray 12.

Figure 12:
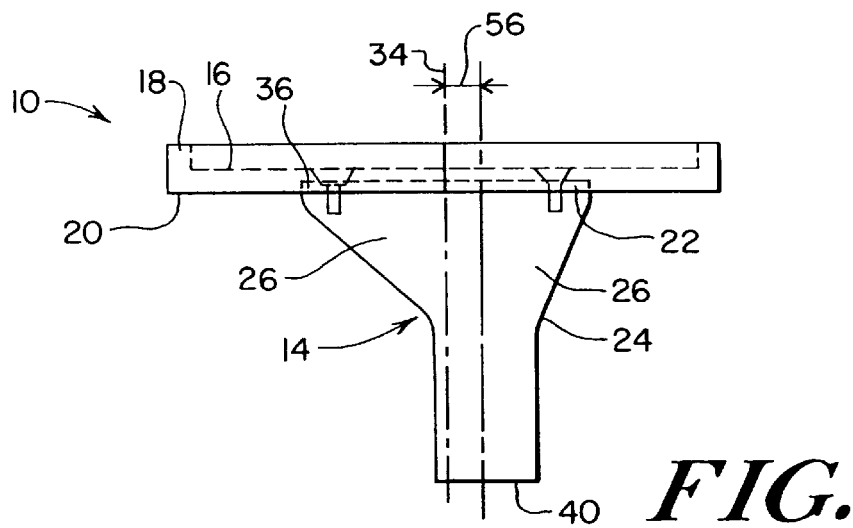
FIG. 12 is an anterior view of a further tibial prosthesis of the invention having an offset modular keel.
Figure 13:
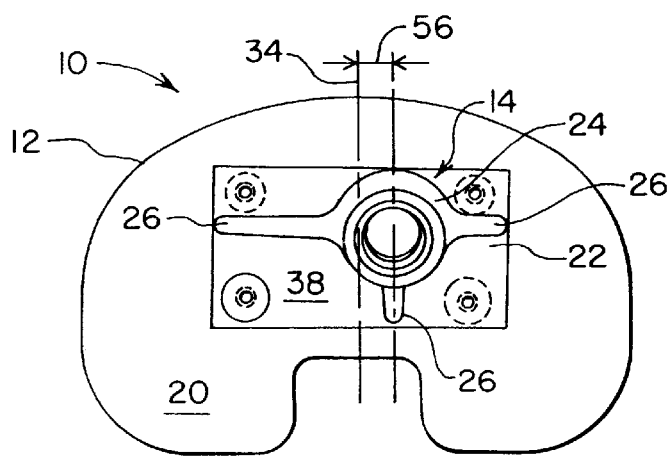
FIG. 13 is an inferior view of the tibial prosthesis of FIG. 12.
Figure 14:
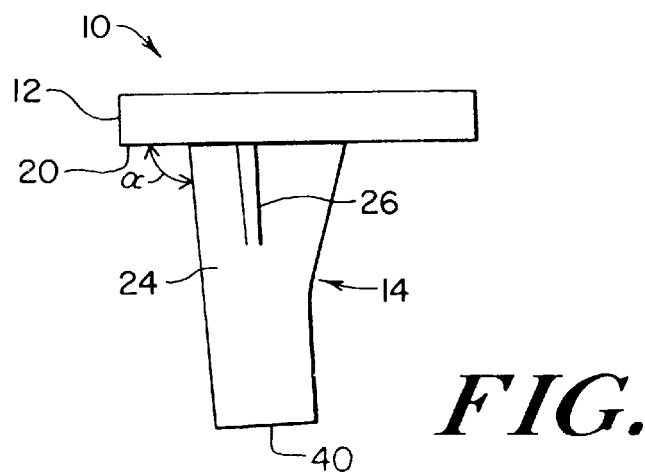
FIG. 14 is a side view of the tibial prosthesis of FIG. 12.

An additional tibial prosthesis 10 having an adjustable keel is illustrated in FIGS. 12 to 14. In this embodiment, the medial-lateral offset 56 is provided on the modular keel 14 itself by offsetting the keel portion 24 in a medial-lateral direction with respect to the tibial tray mating portion 22 of the modular keel 14. Tibial tray mating portion 22 mates with the tibial tray 12 using four screws 32 that are located at fixed positions with respect to the tibial tray 12—though more or fewer screws 32, or other mating elements in place of screws, may be used to attach the offset modular keel 14 to the tibial tray 12. A recessed region 36 may be provided on the inferior surface 20 of the tibial tray 12 having a shape substantially similar to the shape of the tibial tray mating portion 22 of the modular keel 14 and having a depth that results in the inferior surface 38 of the tibial tray mating portion 22 being flush with the inferior surface 20 of the tibial tray 12 when the modular keel 14 is fixed to the tray 12.

In a preferred embodiment, a plurality of modular keels 14 having varying offsets are provided. Typical offsets might include 4, 5, 6, and 8 millimeter offsets in the medial and lateral directions as well as a modular keel having a neutral position (0 millimeter offset). With such an embodiment, a surgeon may adjust keel and stem offsets for a particular patient by selecting an appropriate modular keel from the group of modular keels having different offsets. Where the angle α between the keel portion 24 and the tibial tray 12 in the anterior-posterior plane is 90°, it may be possible to use a single modular keel 14 to provide an offset in either a medial or a lateral direction by reversing the orientation of the modular keel 14.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A tibial prosthesis comprising:
   a tibial tray having a medial-lateral center and an inferior surface matable with a resected proximal tibia; and
   a modular keel comprising a tray mating portion and a keel portion, the keel portion having a plurality of wing elements suitable for anchoring the keel within the proximal tibia, the tray mating portion being fixable to the inferior surface and adjustable in a medial-lateral direction with respect to the medial-lateral center of the tibial tray to allow medial-lateral adjustment of the keel portion with respect to the tray.

2. The prosthesis of claim 1, further comprising a stem receivable within the central canal of a tibia.

3. The prosthesis of claim 2, wherein the stem is modular and matable with the modular keel.

4. The prosthesis of claim 1, wherein the tibial tray includes at least one slot extending in a medial-lateral direction and at least one mating element, fixable to the modular keel, extends through the at least one slot to secure the modular keel to the tibial tray at a preselected offset from the medial-lateral center of the tibial tray.

5. The prosthesis of claim 4, wherein four mating elements secure the modular keel to the tibial tray.

6. The prosthesis of claim 4, wherein one mating element secures the modular keel to the tibial tray.

7. The tibial prosthesis of claim 1, wherein the tibial tray has a superior surface, the prosthesis further comprising a tibial bearing element fixed to the superior surface of the tibial tray.

8. The tibial prosthesis of claim 7, wherein the modular keel is adjustable in the medial-lateral direction with respect to the tibial bearing element.

9. A tibial prosthesis comprising:
   a tibial tray having a medial-lateral center, an inferior surface matable with a resected proximal tibia, two or more slots extending in a medial-lateral direction, and two or more mating elements extending through the two or more slots;
   a modular keel fixable to the inferior surface and adjustable in a medial-lateral direction with respect to the medial-lateral center of the tibial tray;
   wherein the two or more mating elements extend through the two or more slots to secure the modular keel to the tibial tray and fix the medial-lateral position of the keel with respect to the tibial tray.

10. The prosthesis of claim 9, wherein four mating elements secure the modular keel to the tibial tray.

11. The prosthesis of claim 9, further comprising a stem receivable within the central canal of a tibia.

12. The prosthesis of claim 11, wherein the stem is modular and matable with the modular keel.

* * * * *